United States Patent [19]

Celmer et al.

[11] 4,169,887

[45] Oct. 2, 1979

[54] ANTIBIOTICS PRODUCED BY SPECIES OF ACTINOPLANES

[75] Inventors: Walter D. Celmer, New London; Walter P. Cullen, East Lyme; Charles E. Moppett, Mystic; Mark T. Jefferson, Waterford; Liang H. Huang, East Lyme, all of Conn.; Riichjro Shibakawa, Handa; Junsuke Tone, Chita, both of Japan

[73] Assignee: Pfizer Inc., New York, N.Y.

[21] Appl. No.: 930,399

[22] Filed: Aug. 2, 1978

Related U.S. Application Data

[63] Continuation-in-part of Ser. No. 879,607, Feb. 21, 1978, abandoned.

[51] Int. Cl.$^2$ ............................................. A61K 35/00
[52] U.S. Cl. .................................... 424/119; 424/115; 435/128; 435/827
[58] Field of Search .............. 424/119, 115; 195/80 R

[56] References Cited

U.S. PATENT DOCUMENTS 3,852,425  12/1974  Liu et al. ........................... 424/119

Primary Examiner—Jerome D. Goldberg
Attorney, Agent, or Firm—Connolly and Hutz

[57] ABSTRACT

A species of Actinoplanes, designated *Actinoplanes deccanensis* Parenti, Pagani and Beretta subsp. salmoneus Huang subsp. nov., ATCC 31355, when subjected to submerged aerobic fermentation, produces a new antibiotic complex. Methods for the recovery and purification of the antibiotic complex and some of the individual antibiotic components are described.

5 Claims, 2 Drawing Figures

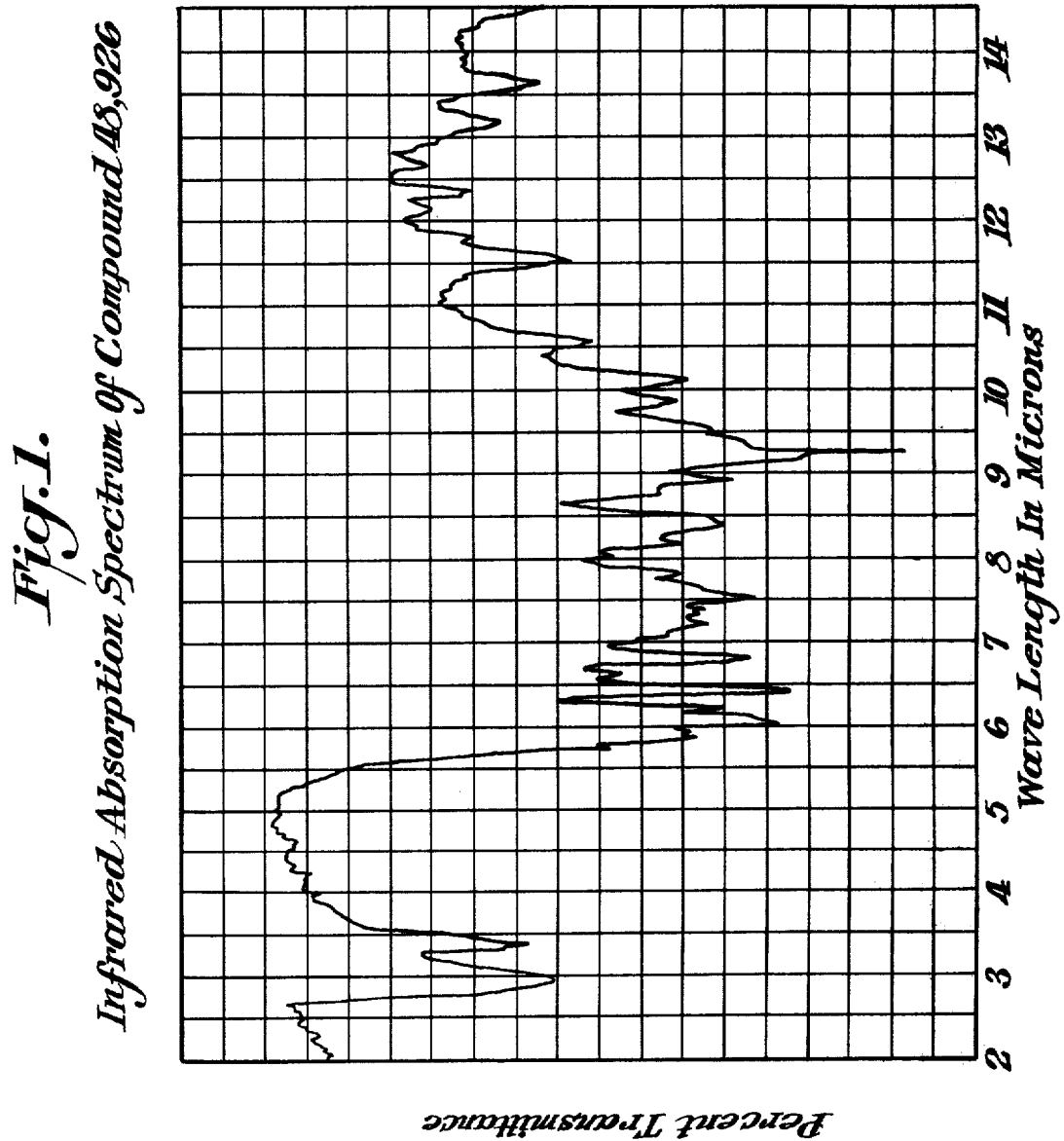

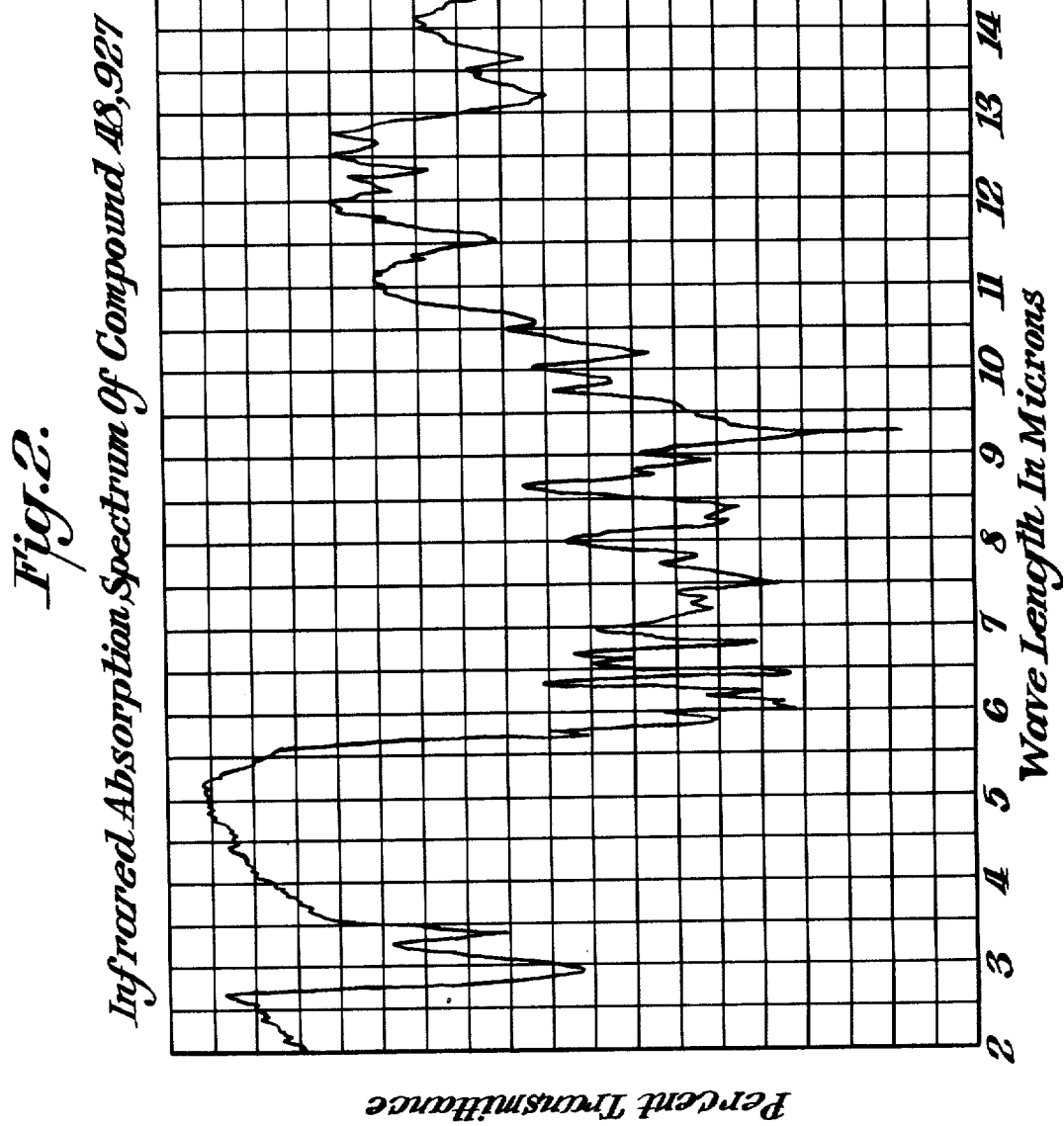

ANTIBIOTICS PRODUCED BY SPECIES OF ACTINOPLANES

CROSS-REFERENCE TO RELATED APPLICATIONS

This application is a continuation-in-part of co-pending U.S. application, Ser. No. 879,607, filed Feb. 21, 1978 now abandoned.

BACKGROUND OF THE INVENTION

The search for new antibiotics produced by soil microorganisms has encompassed the screening of various genera of bacteria and fungi including many species within each genus and many strains within each species.

Among the microorganisms that are receiving growing attention are those that belong to the genus Actinoplanes. This genus is characterized by the production of sporangia and spherical to oval spores that are motile.

SUMMARY OF THE INVENTION

This invention is concerned with Compounds 48,926 and 48,927, acidic antibiotics produced under submerged aerobic fermentation conditions by *Actinoplanes deccanensis* ATCC 31355.

DETAILED DESCRIPTION OF THE INVENTION

The microorganism useful for the preparation of the antibiotics of this invention was isolated from a soil sample from Argentina. This culture has been deposited in The American Type Culture Collection, Rockville, Maryand as the type culture under their accession number ATCC 31355. The permanency of deposit of this culture and ready accessibility thereto by the public are afforded throughout the effective life of the patent. Access to the culture is available during pendency of the application under Rule 14 and 35 USC 112. All restrictions on the availability to the public of the culture deposited will be irrevocably removed upon granting of the patent.

The culture was incubated at 28° C. unless otherwise stated and records of results were made after suitable incubation time (most were at 14 days). Colors were described in common terminology but exact colors were determined by comparison with color chips from the Color Harmony Manual, 4th edition.

Identification media used for the characterization of the culture and references to their compositions are as follows:

1. Tryptone Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium #1, p. 328, 1961.
8. Bennett's Agar—Ibid, medium #30, p. 331.
9. Glucose Asparagine Agar—Ibid, medium #2, p. 328.
10. Glucose-Yeast Extract Agar—Ibid, Medium #29, p. 331.
11. Emerson's Agar—Ibid, medium #28, p. 331.
12. Nutrient Agar—Ibid, medium #14, p. 330.
13. Gordon and Smith' Tyrosine Agar—R. E. Gordon and M. M. Smith, Jr. Bact. 69:147-150, 1955.
14. Casein Agar—Ibid.
15. Calcium Malate Agar—S. A. Waksman, Bact. Rev. 21:1-29, 1957.
16. Gelatin—R. E. Gordon and J. M. Mihm, Jr. Bact. 73:15-27, 1957.
17. Starch—Ibid.
18. Organic Nitrate Broth—Ibid.
19. Dextrose Nitrate Broth—S. A. Waksman, The Actinomycetes, Vol. 2, medium #1, p. 328, 1961, with 3 g dextrose substituted for 30 g sucrose and agar omitted.
20. Potato Carrot Agar—M. P. Lechevalier, Jr. Lab. and Clinical Med. 71:934-944, 1968 but use only 30 g potatoes, 2.5 g carrots and 20 g agar.
21. 2% Tap Water Agar.
22. Peptone Czapek Agar—J. N. Couch, Jr. Elisha Mitchell Soc. 79:53-70, 1963.
23. Skim Milk—Difco.
24. Cellulose utilization—
   (a) H. L. Jensen, Proc. Linn. Soc. N.S.W. 55:231-248, 1930.
   (b) M. Levine and H. W. Schoenlein, A Compilation of Culture Media, medium no. 2511, 1930.
25. Carbohydrates—G. M. Luedemann and B. C. Brodsky, Antimicrobial Agents and Chemotherapy 1964:47, 1965.
26. Temperature Range—ATCC medium 172 in ATCC Culture Collection Catalogue, 12th ed. p. 329, 1976.

The description of the culture is as follows:

Yeast Extract-Malt Extract Agar—Growth good, cream-colored (2 ca) to pale orange (3 ca), raised, wrinkled, no aerial mycelium; reverse same color as surface; soluble pigment pale orange.

Oatmeal Agar—Growth moderate, pale yellowish orange (3 ca) to cream (2 ca), smooth to slightly roughened, thin, no aerial mycelium; reverse same color as surface; no soluble pigment.

Inorganic Salts-Starch Agar—Growth good, pale whitish orange (4 ea), raised, wrinkled, no aerial mycelium; reverse same color as surface; no soluble pigment.

Glycerol-Asparagine Agar—Growth poor to moderate, pale orange (3 ea), thin, appearing a small isolated dots, no aerial mycelium; reverse same color as surface; no soluble pigment.

Gordon and Smith Tyrosine Agar—Growth poor to moderate, pale yellowish orange (4 ea), slightly raised and roughened, no aerial mycelium; reverse same color as surface, with white brownish (5 pg) soluble pigment.

Czapek-Sucrose Agar—Growth moderate, yellowish orange (3 ea), slightly raised, occurring as smooth to isolated dots, no aerial mycelium; reverse same color as surface; no soluble pigment.

Bennett's Agar—Growth good, cream-colored (near 2 ca), raised, wrinkled, no aerial mycelium; reverse same color as surface; no soluble pigment.

Glucose-Asparagine Agar—Growth moderate to good, yellowish orange (near 3 ea), moderately raised, roughened to wrinkled, no aerial mycelium; reverse same color as surface; no soluble pigment.

Calcium Malate Agar—Growth scant, colorless to pale yellowish orange (3 ca), thin, smooth, no aerial mycelium; reverse same color as surface; no soluble pigment.

Casein Agar—Growth good, orange (4 ia), raised, finely wrinkled, no aerial mycelium; reverse same color as surface, with pale orange soluble pigment.

Glucose-Yeast Extract Agar—Growth good, pale yellowish orange (near 3 ea), raised, wrinkled, no aerial mycelium; reverse same color as surface; no soluble pigment.

Emerson's Agar—Growth good, pale pinkish yellow (3 ea), raised, wrinkled, no aerial mycelium; reverse same color as surface; no soluble pigment.

Nutrient Agar—Growth moderate, pale yellowish orange (3 ea), thin to slightly raised, smooth to slightly roughened, no aerial mycelium; reverse same color as surface; no soluble pigment.

Gelatin Agar—Growth moderate to good, yellowish orange (near 4 ia), slightly raised and roughened, no aerial mycelium; reverse same color as surface; no soluble pigment.

Starch Agar—Growth excellent, pale yellowish orange (3 ea). raised, strongly wrinkled, no aerial mycelium; reverse same color as surface; no soluble pigment.

Potato Carrot Agar—Growth moderate, pale yellowish orange (3 ea), thin, smooth to slightly roughened, no aerial mycelium; reverse same color as surface; no soluble pigment.

Tap Water Agar—Growth poor, colorless, thin, smooth, reverse colorless; no soluble pigment.

Peptone Czapek Agar—Growth good, pale yellowish orange (near 3 ea), slightly raised, roughened but wrinkled near the edge of the colony, no aerial mycelium; reverse same color as surface; no soluble pigment.

Biochemical Properties—Melanin not produced, hydrogen sulfide produced; gelatin liquefied; starch hydrolyzed; nitrate reduced to nitrite on both media; poor growth on Levine and Schoenlein's cellulose, good growth on Jensen's cellulose, no decomposition on both cellulose media; coagulation and peptonization on milk; casein digestion positive; no digestion of calcium malate; tyrosine not hydrolyzed. Carbohydrate utilization: glucose, arabinose, fructose, inositol, mannitol, raffinose, rhamnose, sucrose, xylose, cellobiose, galactose, glycerol, lactose, mannose, melibiose, sorbitol, starch, and trehalose utilized; dulcitol, melezitose, ribose, and salicin doubtfully utilized; adonitol, and sorbose not utilized.

Morphological Properties—Morphological observations were made after five to six weeks of incubation of the culture on Calcium Malate Agar; production of sporangia moderate to good on Calcium Malate Agar, poor on Oatmeal Agar, Inorganic Salts-Starch Agar and Potato Carrot Agar; sporangia globose, oval to elongated, with a surface slightly roughened, sessile to short-stalked, 3–7 μm in diameter or 4–7×2-.5–5 μm, often aggregated into clusters; sporangiospores globose to oval, smooth, motile when treated with 1% glucose solution, 1–1.2 μm in diameter or 1.2–1.4×1–1.2 μm.

| Temperature Relations | | | |
| --- | --- | --- | --- |
| 21° C. | 28° C. | 37° C. | 45° C. |
| good growth | good to excellent growth | good growth | no growth |

The *Actinoplanes* culture was found to resemble *Actinoplanes deccanensis* ATCC 21983 in a number of morphological, cultural and biochemical characteristics. It differed, however, in the production of hydrogen sulfide, the ability to utilize sorbitol but not adonitol and melezitose, the positive digestion of casein, the lack of calciummalate digestion and the paler orange colonies on ISP No. 4 Medium, Caclium Malate Agar, Czapek Sucrose Agar and Peptone Czapek Agar. It is considered that the new *Actinoplanes* culture represents a new subspecies of *Actinoplanes deccanensis* and is designated *Actinoplanes deccanensis* Parenti, Pagani and Beretta subsp. *salmoneus* Huang subsp. nov. The sub-specific epithet refers to the color of the substrate mycelium of the organism.

The growth of *Actinoplanes deccanensis* ATCC 31355 preferably takes place in nutrient media at a temperature of about 24° C. to 36° C. and under aerobic, submerged conditions with agitation. Nutrient media which are useful for such purposes include a source of assimilable carbon such as sugars, starch, glycerol and molasses; a source of organic nitrogen such as fish meal, casein, enzymatic digest of casein, meat meal, wheat gluten, cottonseed meal, soybean meal and peanut meal. A source of growth substances such as distillers' solubles and/or yeast extract as well as salts such as sodium chloride, ammonium acetate, ammonium sulfate, potassium phosphate and trace minerals such as iron, manganese, zinc, cobalt and magnesium may also be utilized with advantageous results. If excessive foaming is encountered during fermentation, antifoam agents such as vegetable oils or silicones may be added to the fermentation medium. The pH of the fermentation tends to remain rather constant but if variations are encountered, a buffering agent such as calcium carbonate may also be added to the medium. Aeration of the medium in tanks for submerged growth is preferably maintained at the rate of about ½ to 2 volumes of air per volume of broth per minute. Agitation may be maintained by means of agitators generally familiar to those in the fermentation industry. Aseptic conditions must, of course, be maintained through the transfer of the microorganism and throughout its growth.

Inoculum for the preparation of the antibiotics may be obtained by employing growth from slants or Roux bottles of *A. deccanensis* ATCC 31355, on such agar media as ATCC Medium 172 to which previous reference was made. The growth may be used to inoculate either shake flasks or inoculum tanks, or alternatively, the inoculum tanks may be seeded from the shake flasks. The growth of the microorganism usually reaches its maximum in about 3 or 4 days. However, variations in the equipment used, aeration, rate of stirring, etc. may affect the speed with which the maximum growth is reached. In general, the fermentation is conducted until substantial antimicrobial activity is imparted to the medium, a period of from about 24 hours to about 4 days being sufficient for most purposes.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency.

Thin-layer chromatography employing silica gel is a useful tool for analyzing the antibiotics produced by *A. deccanensis* ATCC 31355, in the fermentation media and the compositions of crude and purified materials extracted from fermentation broths. Silica gel plates are employed with a developing system of chloroform:methanol (9:1 - v/v). Two major antibiotics, Compound 48,926 (less polar) and Compound 48,927 (more polar) and at least three minor antibiotics are apparent by these techniques. Being red pigments these antiobiotics may be observed visually or alternatively they may be visualized by exposure to 254 nm light or biooverlay with agar seeded with a sensitive strain of *Staphylococcus aureus.*

Compounds 48,926 and 48,927 may be recovered and purified by means of solvent extraction and column chromatography. Organic solvents such as n-butanol, methylisobutyl ketone, ethyl acetate and chlorinated hydrocarbons may be used to extract the antibiotics from acidified whole or clarified fermentation broths. The solvent extract may be concentrated to a thin syrup, defatted with heptane and processed with buffer to yield a viscous oil and the oil chromatographed on a silica gel column developed with chloroform containing increasing amounts of methanol.

Antibiotic Compounds 48,926 and 48,927 can be administered via the oral or parenteral routes for the treatment in animals, including humans, of staphylococcal and other antiobiotic-sensitive infections. In general, the antibiotics, or mixtures of antibiotics, are most desirably administered in daily oral doses of 0.5 to 1 gram or parenteral injections of 100 to 500 mg., depending on the type and severity of the infection and weight of the subject being treated.

Antibiotic Compounds 48,926 and 48,927 may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspension and/or elixirs are desired for oral administration, the essential active ingredient(s) therein may be combined with various sweetening or flavoring agents, coloring matter or dyes, and if desired, emulsifying and/or suspending agents as well, together with such diluents as water, ethanol, propylene glycol, glycerol and various combinations thereof.

For purposes of parenteral administration, solutions of Compound 48,926 and 48,927, or mixtures thereof, in sesame or peanut oil or in aqueous propylene glycol may be employed.

EXAMPLE I

A sterile aqueous medium having the following composition was prepared:

| Ingredient | Grams/liter |
| --- | --- |
| Glucose | 10 |
| Starch | 20 |

-continued

| Ingredient | Grams/liter |
| --- | --- |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |
| pH 7.1-7.2 | |

Cells from a slant culture of *A. deccanensis* ATCC 31355 were transferred to each of a number of 300 ml shake flasks each containing 40 ml of the above medium and shaken at 28° C. on a rotary shaker for 3 to 4 days.

A sterile aqueous medium having the following composition was prepared:

| Ingredient | Grams/liter |
| --- | --- |
| Starch | 20 |
| Soy flour | 10 |
| Distillers' solubles | 1 |
| Ferrous sulfate | 0.1 |
| pH 6.0-7.0 | |

Fermentors containing two liters of the above described sterile medium were seeded with 2-4% v/v of grown flask inoculum. The temperature was maintained at 30° C. and the broth was stirred at 1700 r.p.m. and aerated at the rate of about one volume of air per volume of broth per minute. When substantial antiobiotic activity was obtained (2-5 days), the whole or filtered fermentation broth was twice extracted with ⅛ to ¼ volume of methylisobutyl ketone. The separated solvent extract was concentrated in vacuo to a viscous oil.

EXAMPLE II

Growth from the inoculum medium of Example I sufficient to provide about 0.1% v/v of inoculum was transferred to two 2000 gallon fermentors each containing about 1200 gallons of an aqueous nutrient medium of the following composition:

| Ingredient | Grams/liter |
| --- | --- |
| Glucose | 1.0 |
| Enzymatic digest of casein | 2.5 |
| Starch | 5.0 |
| Corn steep liquor | 5 ml |
| Calcium carbonate | 3.0 |
| Cobalt chloride | 0.002 |
| pH 6.0-7.0 | |

The temperature was controlled in the range of 28°-36° C., aeration at the rate of ½ to 2 volumes of air per volume of broth per minute and stirring at 300 to 600 r.p.m. After substantial antibiotic activity was obtained (4-5 days), about 2650 gallons of whole fermentation broth, pH 5.5, was extracted with about 800 gallons of methylisobutyl ketone. The solvent extract was concentrated under vacuum to about 3 liters of an oily extract containing the antibiotic Compounds 48,926, 48,927 and minor components. Trituration with successive 3 gallons, 1.5 gallons and 0.5 gallon of hexane led to 530 grams of a viscous concentrate.

A portion of the above concentrate (265 grams) was dissolved in 2.5 gallons of methylisobutyl ketone and extracted with 2.5 gallons of pH 10.0 disodium hydrogen phosphate buffer (50 grams disodium hydrogen phosphate per liter of water). Care was taken to ensure that the pH of the aqueous phase remained at 10.0. This procedure was repeated with fresh (2.5 gallons) pH 10.0 buffer. The combined aqueous layers were washed with 2.5 gallons of methylisobutyl ketone, the pH of the aqueous phase was adjusted to 4.8 and the desired antibiotics were recovered by extraction twice with successive 1 gallon portions of methylisobutyl ketone. Concentration in vacuo gave 75 grams of a dark red oil. The latter was dispersed on 200 grams of silica gel 60 (E. Merck, Darmstadt, Germany) in the presence of hexane and then added to a sintered glass filter coated with 200 grams of silica gel 60. The silica gel was washed twice with 1 gallon of chloroform, twice with 1 gallon of chloroform:ethanol—97.5:2.5% v/v, 1 gallon of chloroform:ethanol—97:3% v/v, and 1 gallon of chloroform:ethanol—95:5% v/v. The major portion of the antibiotic activity, represented by Compounds 48,926 and 48,927, was found in the first gallon of chloroform:ethanol—97.5:2.5% v/v. This eluate was evaporated in vacuo to afford 7.0 grams of a deep red solid. This material was dispersed on 30 grams of silica gel 60 with the aid of acetone/hexane and added to the top of a column 1"×96 cm packed with silica gel H (E. Merck, Darmstadt, Germany) buffered at pH 5.0 (50 grams sodium dihydrogen phosphate per 1.0 liter of water, 1.0 liter of buffer per kilo of silica gel H, dried overnight ca. 125° C.). The column was developed with hexane containing increasing amounts of chloroform followed by chloroform containing increasing amounts of methanol up to chloroform:methanol 96:4 v/v. Appropriate cuts from this column were combined to afford substantially pure Compound 48,926 (980 mg) and Compound 48,927 (760 mg). Intermediate cuts were approximately 50:50 mixture of the two antibiotics. Analytical samples of Compound 48,926 and Compound 48,927 were derived by further chromatography on pH 5.0 buffered silica gel H developed with hexane, hexane: chloroform, chloroform and chloroform:methanol—99:1 for Compound 48,926 and chloroform:ethanol—99.5:0.5 for Compound 48,927. These antibiotics were obtained as amorphous deep red solids.

Compound 48,926 (sample dried overnight in vacuo at 52° C.) has an average composition by weight of 55.76% carbon, 5.39% hydrogen, 5.36% nitrogen and 33.49% oxygen (by difference).

Compound 48,926 is optically active having a rotation of $[\alpha]_D = +413°$ (c=0.097, CHCl$_3$). Its ultraviolet light absorption maxima in methanol occur at 211, 218$_{sh}$, 240$_{sh}$, 295$_{sh}$, 304 and 500 nm with E$_1$ $_{cm}$$^{1\%}$ values of 615, 543, 313, 322, 339 and 17, respectively.

The infrared spectrum of Compound 48,926, FIG. 1, is attached. A KBr pellet shows characteristic absorption of the infrared region at the following wavelengths in microns: 2.93, 3.38, 5.74, 5.87, 5.95, 6.03, 6.23, 6.42, 6.82, 7.50 and 8.40.

Compound 48,926 is soluble in chloroform, ethyl acetate and methylisobutyl ketone; insoluble in heptane, hexane and water.

Compound 48,927 (sample dried overnight in vacuo at 52° C.) has an average composition by weight of 55.03% carbon, 4.95% hydrogen, 5.06% nitrogen and 34.96% oxygen (by difference).

Compound 48,927 is optically active having a rotation of $[\alpha]_D = +513°$ (c=0.101, CHCl$_3$). Its ultraviolet light absorption maxima in methanol occurs at 240$_{sh}$, 296$_{sh}$, 303 and 500 nm with E$_1$ $_{cm}$$^{1\%}$ values of 338, 358, 367 and 20, respectively.

The infrared spectrum of Compound 48,927, FIG. 2, is attached. A KBr pellet shows characteristic absorption in the infrared region at the following wavelengths in microns: 2.94, 3.39, 5.74, 5.90, 6.04, 6.12, 6.24, 6.80, 7.50, 8.40 and 10.20.

Compound 48,927 is soluble in chloroform, ethyl acetate and methylisobutyl ketone; insoluble in heptane, hexane and water.

What is claimed is:

1. The antibiotic Compound 48,926 which is soluble in chloroform, ethyl acetate and methylisobutyl ketone; insoluble in heptane, hexane and water; has an optical rotation of $[\alpha]_D = +413°$ at a concentration of 0.097% in chloroform; an average composition by weight of 55.76% carbon, 5.39% hydrogen, 5.36% nitrogen and 33.49% oxygen (by difference); absorption maxima in methanol in the ultraviolet light region of the spectrum at 211, 218$_{sh}$, 240$_{sh}$, 295$_{sh}$, 304 and 500 nm with E$_1$ $_{cm}$$^{1\%}$ values of 615, 543, 313, 322, 339 and 17, respectively; and when pelleted in KBr, exhibits characteristic absorption in the infrared region at the following wavelengths in microns: 2.93, 3.38, 5.74, 5.87, 5.95, 6.03, 6.23, 6.42, 6.82, 7.50 and 8.40.

2. The antibiotic Compound 48,927 which is soluble in chloroform, ethyl acetate and methylisobutyl ketone; insoluble in heptane, hexane and water; has an optical rotation of $[\alpha]_D = +513°$ at a concentration of 0.101% in chloroform; an average composition by weight of 55.03% carbon, 4.95% hydrogen, 5.06% nitrogen and 34.96% oxygen (by difference); absorption maxima in methanol in the ultraviolet light region of the spectrum at 240$_{sh}$, 296$_{sh}$, 303 and 500 nm with E$_1$ $_{cm}$$^{1\%}$ values of 338, 358, 367 and 20, respectively; and when pelleted in KBr, exhibits characteristic absorption in the infrared region at the following wavelengths in microns: 2.94, 3.39, 5.74, 5.90, 6.04, 6.12, 6.24, 6.80, 7.50, 8.40 and 10.20.

3. A process for producing an antibiotic complex which comprises cultivating the microorganism *A. deccanensis* ATCC 31355 in aqueous culture media containing an assimilable source of carbon, nitrogen and inorganic salts until substantial antibiotic activity is obtained.

4. The antibiotic complex produced by the process of claim 3.

5. A process according to claim 3 wherein said antibiotic complex is separated from the fermentation medium.

* * * * *